United States Patent
Sechrist et al.

(10) Patent No.: US 12,077,800 B2
(45) Date of Patent: Sep. 3, 2024

(54) LIQUID DISTRIBUTOR SYSTEM AND PROCESS OF LIQUID DISTRIBUTION

(71) Applicant: LanzaTech, Inc., Skokie, IL (US)

(72) Inventors: Paul Alvin Sechrist, South Barrington, IL (US); Bjorn Daniel Heijstra, Bergen (NL); Joshua Jeremy Conolly, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 68 days.

(21) Appl. No.: 17/807,309

(22) Filed: Jun. 16, 2022

(65) Prior Publication Data
US 2023/0407345 A1    Dec. 21, 2023

(51) Int. Cl.
| | | |
|---|---|---|
| C12M 3/00 | (2006.01) | |
| C12M 1/00 | (2006.01) | |
| C12P 7/00 | (2006.01) | |
| C12P 7/04 | (2006.01) | |

(52) U.S. Cl.
CPC ............ C12P 7/04 (2013.01); C12M 29/06 (2013.01); C12M 29/18 (2013.01); C12M 29/24 (2013.01)

(58) Field of Classification Search
CPC ............................ C12M 23/40; C12M 29/06
See application file for complete search history.

(56) References Cited

U.S. PATENT DOCUMENTS

| | | | |
|---|---|---|---|
| 3,618,779 A * | 11/1971 | Goodman | C02F 3/1242 |
| | | | 210/221.1 |
| 5,122,312 A | 6/1992 | Tomalesky | |
| 5,342,781 A * | 8/1994 | Su | C12M 27/20 |
| | | | 435/813 |
| 6,492,135 B1 | 12/2002 | Larsen | |
| 7,972,824 B2 | 7/2011 | Simpson | |
| 8,293,509 B2 | 10/2012 | Simpson | |
| 8,658,408 B2 | 2/2014 | Simpson | |

(Continued)

FOREIGN PATENT DOCUMENTS

| | | |
|---|---|---|
| CN | 205948388 U | 2/2017 |
| WO | 2012015317 A1 | 2/2012 |

(Continued)

OTHER PUBLICATIONS

Drake, Acetogenic Prokaryotes, In: The Prokaryotes, 3rd edition, p. 354, New York, NY, 2006.

(Continued)

*Primary Examiner* — Nathan A Bowers

(57) ABSTRACT

The disclosure provides a system and a process for injecting and uniformly distributing a liquid into a fermentation broth in a bioreactor for maintaining stable condition within the fermentation broth. The system includes a downcomer section which contains two or more circular pipe conduits extending from a wall of the downcomer to the center vertical axis line of the downcomer. Liquid injection apertures are arranged along the circular pipe conduit and are non-uniformly spaced apart from the center vertical axis of the downcomer to the wall of the downcomer. The apertures further alternate and are offset between the top and bottom surfaces of the circular pipe conduit. The process of the disclosure involves using the system described above for carrying out a fermentation process for converting a C1-substrate to at least one product such as ethanol.

13 Claims, 5 Drawing Sheets

(56) References Cited

U.S. PATENT DOCUMENTS

| | | |
|---|---|---|
| 8,900,836 B2 | 12/2014 | Simpson |
| 9,068,202 B2 | 6/2015 | Tran |
| 9,284,564 B2 | 3/2016 | Mueller |
| 9,347,076 B2 | 5/2016 | Liew |
| 9,359,611 B2 | 6/2016 | Koepke |
| 9,410,130 B2 | 8/2016 | Koepke |
| 9,738,875 B2 | 8/2017 | Koepke |
| 9,890,384 B2 | 2/2018 | Mueller |
| 9,994,878 B2 | 6/2018 | Koepke |
| 10,174,303 B2 | 1/2019 | Behrendorff |
| 10,590,406 B2 | 3/2020 | Koepke |
| 10,913,958 B2 | 2/2021 | Koepke |
| 2009/0068727 A1* | 3/2009 | Karr ............... C12M 21/02 435/292.1 |
| 2011/0244538 A1 | 10/2011 | Trevethick |
| 2012/0045807 A1 | 2/2012 | Simpson |
| 2013/0157322 A1 | 6/2013 | Simpson |
| 2017/0087528 A1 | 3/2017 | Pretz |
| 2019/0185888 A1 | 6/2019 | Koepke |
| 2021/0047596 A1* | 2/2021 | O'Neal ............... C12M 27/04 |
| 2021/0292732 A1 | 9/2021 | Liew |
| 2023/0062038 A1* | 3/2023 | Liu ............... H01L 21/67017 |

FOREIGN PATENT DOCUMENTS

| | | |
|---|---|---|
| WO | 2014204326 A1 | 12/2014 |
| WO | 2015016722 A1 | 2/2015 |

OTHER PUBLICATIONS

Ragsdale, Biochim Biophys Acta, 1784: 1873-1898, 2008.

International Search Report and Written Opinion issued in corresponding International Application No. PCT/US2023/025146, dated Oct. 4, 2023, 13 pages.

\* cited by examiner

LIQUID DISTRIBUTOR SYSTEM AND PROCESS OF LIQUID DISTRIBUTION

FIELD

The disclosure relates to a device and associated process for distributing one or more liquids such as chemicals and/or nutrients to a bioreactor. In particular, the disclosure relates to the use of a liquid distributor for distributing the liquid into the fermentation broth contained within the bioreactor. The liquid distributor allows uniform distribution of the liquid into the fermentation broth and minimizes localized high concentration of the liquid.

BACKGROUND

Carbon dioxide ($CO_2$) accounts for about 76% of global greenhouse gas emissions from human activities, with methane (16%), nitrous oxide (6%), and fluorinated gases (2%) accounting for the balance (United States Environmental Protection Agency). The Majority of $CO_2$ comes from the burning fossil fuels to produce energy. Reduction of greenhouse gas emissions, particularly $CO_2$, is critical to halt the progression of global warming and the accompanying shifts in climate and weather.

It has long been recognized that catalytic processes, such as the Fischer-Tropsch process, may be used to convert gases containing carbon dioxide ($CO_2$), carbon monoxide (CO), and/or hydrogen ($H_2$), such as industrial waste gas or syngas or mixtures thereof into a variety of chemicals such as ethanol, acetone, and isopropanol. Syngas can also be converted to various chemicals by the Monsanto process by converting to methanol as a first step. Both the Fischer-Tropsch and the Methanol synthesis units are optimized at very high capacities. They require well defined feed gas compositions and syngas feed with low impurities to avoid poisoning the catalysts. The Fischer-Tropsch process requires complex and costly purification equipment to generate high purity industrial chemicals.

Gas fermentation has emerged as an alternative platform for biological fixation of carbon in gases containing a single carbon atom such as carbon monoxide (CO), carbon dioxide ($CO_2$), and/or methane ($CH_4$). In particular, the C1-fixing microorganisms act as biocatalysts to convert a C1-carbon substrate or source into valuable fermentation products such as ethanol or other C1-C4 alcohols. The "C1-carbon source or substrate" refers to a one carbon-molecule that serves as a partial or sole carbon source for the microorganism. For example, the C1-carbon substrate or source may comprise one or more of CO, $CO_2$, $CH_4$, $CH_3OH$, or $CH_2O_2$. In an embodiment, the C1-carbon source or substrate comprises one or both of CO and $CO_2$.

Biological processes, such as gas fermentation processes require the addition of liquids such as nutrients and chemicals to maintain stable operating conditions across the bioreactor. One challenge in adding or injecting such liquids into a large volume of fermentation broth is to uniformly distribute and mix the liquid into the broth. If the liquid is maldistributed, high concentration zones of the liquid can develop in a small area of the bioreactor i.e., broth, which will take time to disperse and become uniformly distributed. For example, if a base such as KOH is to be added to adjust the pH of the broth, the pH of the fermentation broth at the injection point can be much lower than in the rest of the fermentation broth until the injected base has a chance to disperse throughout the broth. This sudden change in pH can affect the viability of the microorganisms around this localized area. Similarly, if a liquid containing nutrients is to be injected, it will take more time for the microorganisms further from the injection point to receive nutrients thus stressing the microorganisms.

Accordingly, there remains a need for a system to inject a liquid into a bioreactor which provides a substantially uniform distribution of that liquid.

SUMMARY

In one embodiment of the disclosure, a bioreactor system comprises (i) a riser section (ii) a downcomer section in fluid communication with the riser section; (iii) at least two liquid distributors each comprising a circular pipe conduit longitudinally extending from a wall of the downcomer section to a center vertical axis of the downcomer section and terminating at a closed end proximate to a center vertical axis of the downcomer section; and (iv) the circular pipe conduit comprising a plurality of liquid injection apertures along the circular pipe conduit beginning at a proximal end from the center vertical axis and terminating at a distal end from the center vertical axis, the liquid injection apertures arranged such that the spacing between successive apertures decreases non-uniformly along the length of the circular pipe conduit from the proximal end of the center vertical axis of the downcomer section to the distal end of the center vertical axis of the downcomer section. The liquid injection apertures are positioned in a plane perpendicular to the center vertical axis of the downcomer section. In some embodiment, each of the liquid injection aperture opening is from about 3 mm to about 11 mm. In some other embodiment, the number of apertures in the circular pipe conduit varies from 4 to 10 apertures. In one aspect, the downcomer section comprises two liquid distributors radially spaced apart at about 180 degrees from each other. In another aspect, the downcomer section comprises four liquid distributors radially spaced apart at about 90 degrees from each other.

In another embodiment of the disclosure, a liquid distributor comprises a circular pipe conduit comprising a plurality of liquid injection apertures, the conduit comprising a closed end and a connector end wherein the liquid injection apertures are arranged from the closed end of the circular pipe conduit to the connector end of the circular pipe conduit, the spacing between successive apertures decreases non-uniformly from the closed end to the connector end of the circular pipe conduit.

In yet another embodiment of the disclosure, a fermentation process comprises (a) fermenting a C1-containing gaseous substrate in a bioreactor having a culture of one or more C1 fixing microorganisms to produce a fermentation broth comprising at least one fermentation product; (b) circulating the fermentation broth from a riser section of the bioreactor and then through a downcomer section of the bioreactor; and (c) injecting at least one liquid into the fermentation broth through at least two liquid distributor, each liquid distributor comprising (i) a circular pipe conduit longitudinally extending from a wall of the downcomer section to a center vertical axis of the downer section and terminating at a closed end proximate to the center vertical axis of the downcomer section; (ii) the circular pipe conduit comprising a plurality of liquid injection apertures along the circular pipe conduit beginning at a proximal end from the center vertical axis and terminating at a distal end from the center vertical axis; (iii) the liquid injection apertures arranged such that the spacing between successive apertures decreases non-uniformly along the circular pipe conduit from the proximal end of the center vertical axis of the downer section to the distal end of the center vertical axis of the downer section; and (iv) the liquid injection apertures arranged such that the stream exiting one aperture covers an annular area substantially equal to the annular area covered by a successive aperture. In some embodiment, each of the liquid injection aperture injects the liquid at an exit velocity in the range from about 0.5 m/s to about 1.2 m/s. In some other embodiment, the liquid is selected from $NH_4OH$, KOH, nutrients, phosphoric acid, or any combinations thereof.

In yet another embodiment of the disclosure, a bioreactor system comprises a (i) riser section (ii) a downcomer section in fluid communication with the riser section; and (iii) a liquid distributor comprising a circular pipe conduit attached to a downcomer section wall and longitudinally extending from the downcomer section wall across substantially the entire diameter of the downcomer and terminating at a closed end and secured to a support member attached to a downcomer section wall proximate to the to the closed end (iv) the circular pipe conduit comprising a plurality of liquid injection apertures along the circular pipe conduit beginning at a midpoint of the circular pipe conduit, corresponding to the center vertical axis of the downcomer section, the liquid injection apertures arranged such that the spacing between successive liquid injection apertures decreases non-uniformly along the length of the circular pipe conduit from the midpoint of the circular pipe conduit to both the closed end of the circular pipe conduit and to the downcomer section wall to which the conduit is attached.

DETAILED DESCRIPTION

Figure 1A:
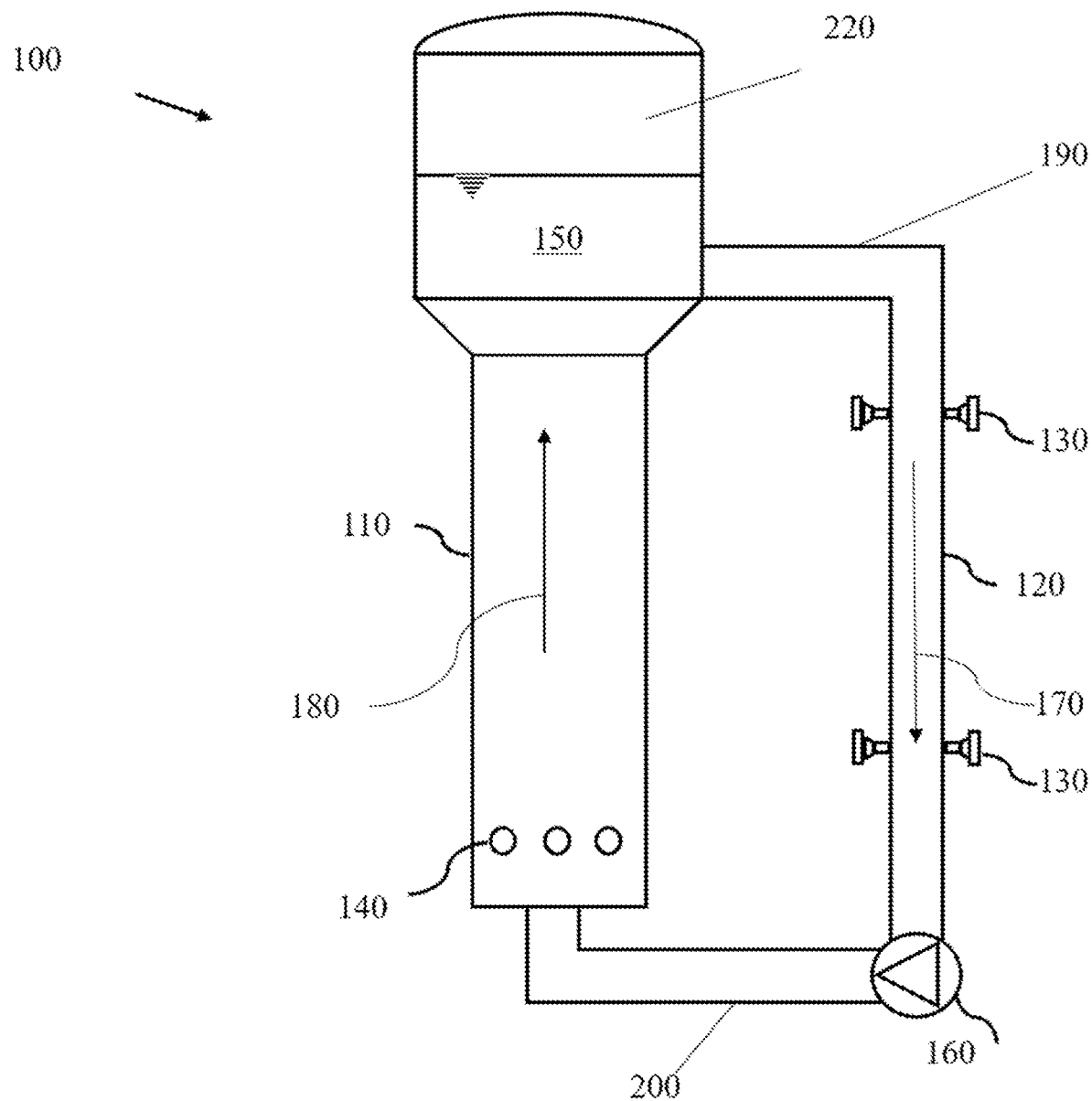
FIG. 1A shows a bioreactor system comprising a riser section, a downcomer section, and the liquid distributors in accordance with one embodiment of the disclosure.

Injecting a liquid such that it's substantially uniformly distributed into a bioreactor containing a fermentation broth prevents formation of localized concentration zones of such liquid in the bioreactor and therefore increases viability of the microorganisms present within the broth, which in turn enhances efficiency of the fermentation process. The disclosure is directed to embodiments of various systems for effecting the injection of liquids and the uniform distribution of the liquids throughout the bioreactor The term "bioreactor" includes a fermentation device consisting of one or more vessels and/or towers or piping arrangements which includes, continuous stirred tank reactor, immobilized cell reactor, trickle bed reactor, bubble column, gas lift fermenter, static mixer, circulated loop reactor, membrane reactor, such as a hollow fibre membrane bioreactor, or other vessel or other device suitable for a gas-liquid contact. A bioreactor receives a gaseous substrate comprising at least one of CO, $CO_2$, $H_2$, or any mixtures thereof. The bioreactor may also comprise a system of multiple reactors (stages) either in parallel or in series. For example, the bioreactor may comprise a first growth reactor which cultures the microorganism and a second fermentation reactor to which output from the growth reactor may be fed and produce most of the fermentation products. In some embodiments, multiple bioreactors in a bioreactor system are placed on top of another to form a stack. A stack of bioreactors improve throughput of the bioreactor system without significantly increasing demand for land area. In some embodiments, the bioreactors include microbubble bioreactors having mechanisms to substantially improve rate of the gas-liquid mass transfer without increasing energy consumption.

"C1 comprising gaseous substrate" means a carbon and/or energy source for the microorganism(s) described herein. By "C1 comprising" is meant a one carbon compound such as CO, $CO_2$, $CH_4$, $CH_3OH$, and $CH_2O_2$. In an embodiment, the C1 comprising gaseous substrate comprises one or both of CO and $CO_2$. In addition to the C1-compounds, the C1 comprising gaseous substrate may further comprise other non-carbon components, such as $H_2$, $N_2$, or electrons. The C1 comprising gaseous substrate can be a gas obtained as a by-product of an industrial process or from another source, such as combustion engine exhaust fumes, biogas, landfill gas, direct air capture, flaring, or from electrolysis. The C1 comprising gaseous substrate can be syngas generated by pyrolysis, torrefaction, or gasification. In other words, carbon in solid or liquid materials may be recycled by pyrolysis, torrefaction, or gasification to generate syngas which is used as the C1 comprising gaseous substrate in gas fermentation. The C1 comprising gaseous substrate source can be natural gas. The C1 comprising gaseous substrate can be carbon dioxide from conventional and unconventional gas production. The C1 comprising substrate can be a gas comprising methane. Gas fermentation processes are flexible and any of these C1 comprising gaseous substrates can be employed.

In certain embodiments, the industrial process source of the C1 comprising gaseous substrate is selected from ferrous metal products manufacturing, such as a steel manufacturing, non-ferrous products manufacturing, petroleum refining, electric power production, carbon black production, paper and pulp manufacturing, ammonia production, methanol production, coke manufacturing, petrochemical production, carbohydrate fermentation, cement making, aerobic digestion, anaerobic digestion, catalytic processes, natural gas extraction, cellulosic fermentation, oil extraction, industrial processing of geological reservoirs, processing fossil resources such as natural gas coal and oil, landfill operations, or any combination thereof. Examples of specific processing steps within an industrial process include catalyst regeneration, fluid catalyst cracking, and catalyst regeneration. Air separation and direct air capture are other suitable industrial processes. Specific examples in steel and ferroalloy manufacturing include blast furnace gas, basic oxygen furnace gas, coke oven gas, direct reduction of iron furnace top-gas, and residual gas from smelting iron. Other general examples include flue gas from fired boilers and fired heaters, such as natural gas, oil, or coal fired boilers or heaters, and gas turbine exhaust. Another example is the flaring of compounds such as at oil and gas production sites. In these embodiments, the C1 comprising gaseous substrate may be captured from the industrial process before it is emitted into the atmosphere, using any known method.

The C1 comprising gaseous substrate can be synthesis gas known as syngas, which may be obtained from reforming, partial oxidation, plasma, or gasification processes. Examples of gasification processes include gasification of coal, gasification of refinery residues, gasification of petroleum coke, gasification of biomass, gasification of lignocellulosic material, gasification of waste wood, gasification of black liquor, gasification of municipal solid waste, gasification of municipal liquid waste, gasification of industrial solid waste, gasification of industrial liquid waste, gasification of refuse derived fuel, gasification of sewerage, gasification of sewerage sludge, gasification of sludge from wastewater treatment, gasification of landfill gas, gasification of biogas such as when biogas is added to enhance gasification of another material. Examples of reforming processes include, steam methane reforming, steam naphtha reforming, reforming of natural gas, reforming of biogas, reforming of landfill gas, reforming of coke oven gas, reforming of pyrolysis off-gas, reforming of ethylene production off-gas, naphtha reforming, and dry methane reforming. Examples of partial oxidation processes include thermal and catalytic partial oxidation processes, catalytic partial oxidation of natural gas, partial oxidation of hydrocarbons, partial oxidation of biogas, partial oxidation of landfill gas, or partial oxidation of pyrolysis off-gas. Examples of municipal solid waste include tires, plastics, refuse derived fuel, and fibers such as in carpeting, shoes, apparel, and textiles.

The syngas substrate generally contains a major proportion of CO, such as at least about 15% to about 75% CO by volume, from about 20% to about 70% CO by volume, from about 20% to about 65% CO by volume, from about 20% to about 60% CO by volume, and from about 20% to about 55% CO by volume. In some embodiments, the syngas substrate comprises about 25% CO, or about 30% CO, or about 35% CO, or about 40% CO, or about 45% CO, or about 50% CO, or about 55% CO, or about 60% CO by volume.

The C1-fixing microorganisms in accordance with the disclosure is selected from *Clostridium, Moorella, Pyrococcus, Eubacterium, Desulfobacterium, Carboxydothermus, Acetogenium, Acetobacterium, Acetoanaerobium, Butyribaceterium, Peptostreptococcus* and mixtures thereof. The microorganisms in the bioreactor may be a modified microorganism derived from a naturally occurring or parental microorganism. A "parental microorganism" is a microorganism from which another microorganism can be derived. Both the parental and derived microorganism are microorganisms of the disclosure. The parental microorganism may be a naturally-occurring microorganism (i.e., a wild-type microorganism) or a microorganism previously modified (i.e., an optimized, a mutant or recombinant microorganism). Microorganisms of the disclosure may be modified to express or overexpress one or more enzymes that were not expressed or overexpressed in the parental microorganism. Similarly, microorganisms of the disclosure may be modified to contain one or more genes that were not contained in the parental microorganism. Microorganisms of the disclosure may also be modified to not express or to express lower amounts of one or more enzymes that were expressed in the parental microorganism. In accordance with one embodiment, the microorganism is selected from or derived from *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides, Cupriavidus necator, Thermoanaerobacter kivui*, and any combinations thereof. In one embodiment, the microorganism of the invention is selected from or derived from *Clostridium autoethanogenum, Clostridium ljungdahlii*, or *Clostridium ragsdalei*. In one embodiment, the parental microorganism is *Clostridium autoethanogenum* LZ1561 which was deposited on Jun. 7, 2010, with Deutsche Sammlung von Mikroorganismen and Zellkulturen GmbH (DSMZ) located at Inhoffenstraße 7B, D-38124 Braunschweig, under the terms of the Budapest Treaty and accorded accession number DSM23693. This strain is described in International Patent Application No. PCT/NZ2011/000144, which is published as WO 2012/015317.

"Wood-Ljungdahl" refers to the Wood-Ljungdahl pathway of carbon fixation as described, i.e., by Ragsdale, *Biochim Biophys Acta*, 1784: 1873-1898, 2008. "Wood-Ljungdahl microorganisms" refers, predictably, to microorganisms containing the Wood-Ljungdahl pathway. Generally, the microorganism of the invention contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert CO, $CO_2$, and/or $H_2$ to acetyl-CoA.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5 vol. % oxygen). Typically, the microorganism of the invention is an anaerobe.

"Acetogens" are obligately anaerobic bacteria that use the Wood-Ljungdahl pathway as their main mechanism for energy conservation and for the synthesis of acetyl-CoA and acetyl-CoA-derived products, such as acetate (Ragsdale, *Biochim Biophys Acta*, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, 3$^{rd}$ edition, p. 354, New York, NY, 2006). All naturally occurring acetogens are C1-fixing, anaerobic, autotrophic, and non-methanotrophic. Typically, the microorganism of the invention is an acetogen.

An "ethanologen" is a microorganism that produces or is capable of producing ethanol. Typically, the microorganism of the invention is an ethanologen.

An "autotroph" is a microorganism capable of growing in the absence of organic carbon. Instead, autotrophs use inorganic carbon sources, such as CO and/or $CO_2$. Typically, the microorganism of the invention is an autotroph.

A "carboxydotroph" is a microorganism capable of utilizing CO as a sole source of carbon and energy. Typically, the microorganism of the invention is a carboxydotroph.

"Nutrient media" or "Nutrient medium" is used to describe bacterial growth media. Generally, this term refers to a media containing nutrients and other components appropriate for the growth of a microbial culture. The term "nutrient" includes any substance that may be utilized in a metabolic pathway of a microorganism. Exemplary nutrients include potassium, B vitamins, trace metals, and amino acids.

The term "inoculum" is intended to encompass the fermentation broth initially grown in an inoculation reactor which is then passed to the one or more subsequent bioreactors to seed the one or more subsequent bioreactor. Preferably, the inoculum is utilized by the one or more bioreactors to produce one or more fermentation product.

The term "fermentation broth" or "broth" is intended to encompass the mixture of components including nutrient media and a culture or one or more microorganisms. It should be noted that the term microorganism and the term bacteria are used interchangeably throughout the document.

Unless the context requires otherwise, the phrases "fermenting", "fermentation process" or "fermentation reaction" and the like, as used herein, are intended to encompass both the growth phase and product biosynthesis phase of the gaseous substrate The culture/fermentation occurs under appropriate environmental conditions of the bioreactor for production of certain target fermentation products. Generally, culture/fermentation is performed under anaerobic conditions. Reaction conditions for carrying out the fermentation of C1-containing substrates in the bioreactor include, without limitation, temperature, gas flow rate, fermentation broth flow rate, pH of the fermentation broth, inoculum level, maximum gas substrate concentration, and adequate supply of the nutrients, to ensure that the fermentation product output is maximized. Stability of such reaction conditions is important for successful gas fermentation to produce the fermentation product. The microorganisms act as biocatalysts that may be cultured with the substrate for gas fermentation to produce one or more fermentation products. For instance, the microorganisms of the disclosure may produce or may be engineered to produce fermentation product for example, ethanol (WO 2007/117157), acetate (WO 2007/117157), 1-butanol (WO 2008/115080, WO 2012/053905, and WO 2017/066498), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (WO 2012/024522 and WO 2013/185123), ethylene (WO 2012/026833), acetone (WO 2012/115527), isopropanol (WO 2012/115527), lipids (WO 2013/036147), 3-hydroxypropionate (WO 2013/180581), terpenes, (WO 2013/180584), fatty acids (WO 2013/191567), 2-butanol (WO 2013/185123), 1,2-propanediol (WO 2014/036152), 1-propanol (WO 2017/066498), 1-hexanol (WO 2017/066498), 1-octanol (WO 2017/066498), chorismate-derived products (WO 2016/191625), 3-hydroxybutyrate (WO 2017/066498), 1,3-butanediol (WO 2017/066498), 2-hydroxyisobutyrate (WO 2017/066498), isobutylene (WO 2017/066498), adipic acid (WO 2017/066498), 1,3-hexanediol (WO 2017/066498), 3-methyl-2-butanol (WO 2017/066498), 2-buten-1-ol (WO 2017/066498), isovalerate (WO 2017/066498), isoamyl alcohol (WO 2017/066498), monoethylene glycol (WO 2019/126400) and combinations thereof.

A "native product" is a product produced by a genetically unmodified microorganism. For example, ethanol, acetate, and 2,3-butanediol are native products of Clostridium autoethanogenum, Clostridium ljungdahlii, and Clostridium ragsdalei. A "non-native product" is a product that is produced by a genetically modified microorganism but is not produced by a genetically unmodified microorganism from which the genetically modified microorganism is derived.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time, in turn, dictates the required volume of a bioreactor, the use of pressurized systems can greatly reduce the volume of the bioreactor required, and consequently the capital cost of the fermentation equipment.

Target products may be separated or purified from a fermentation broth using any method or combination of methods known in the art, including, for example, fractional distillation, evaporation, pervaporation, gas stripping, phase separation, and extractive fermentation, including, for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor.

FIG. 1A shows a bioreactor system in accordance with one embodiment of the disclosure. The bioreactor system 100 shows a circulated loop bioreactor that includes a riser section 110 where a liquid and a gas flow concurrently in an upward direction 180, and a downcomer section 120 where the liquid and the gas flow concurrently in a downward direction 170. The riser section 110 and the downcomer section 120 are fluidically connected via two horizontal sections 190, 200. Multiple spargers 140 introduce the C1-containing gaseous substrate into the bioreactor system 100. At least one circulating pump 160 positioned at a bottom portion of the downcomer section 120 drives two phase flow having gas-liquid mixture. A portion of the gaseous substrate is carried over into the downcomer section 120 after separating from the fermentation broth 150 in a gas headspace 220. Accordingly, the liquid and the gas mixture flows from the riser section 110 to the downcomer section 120 and back forming a loop.

Figure 1B:
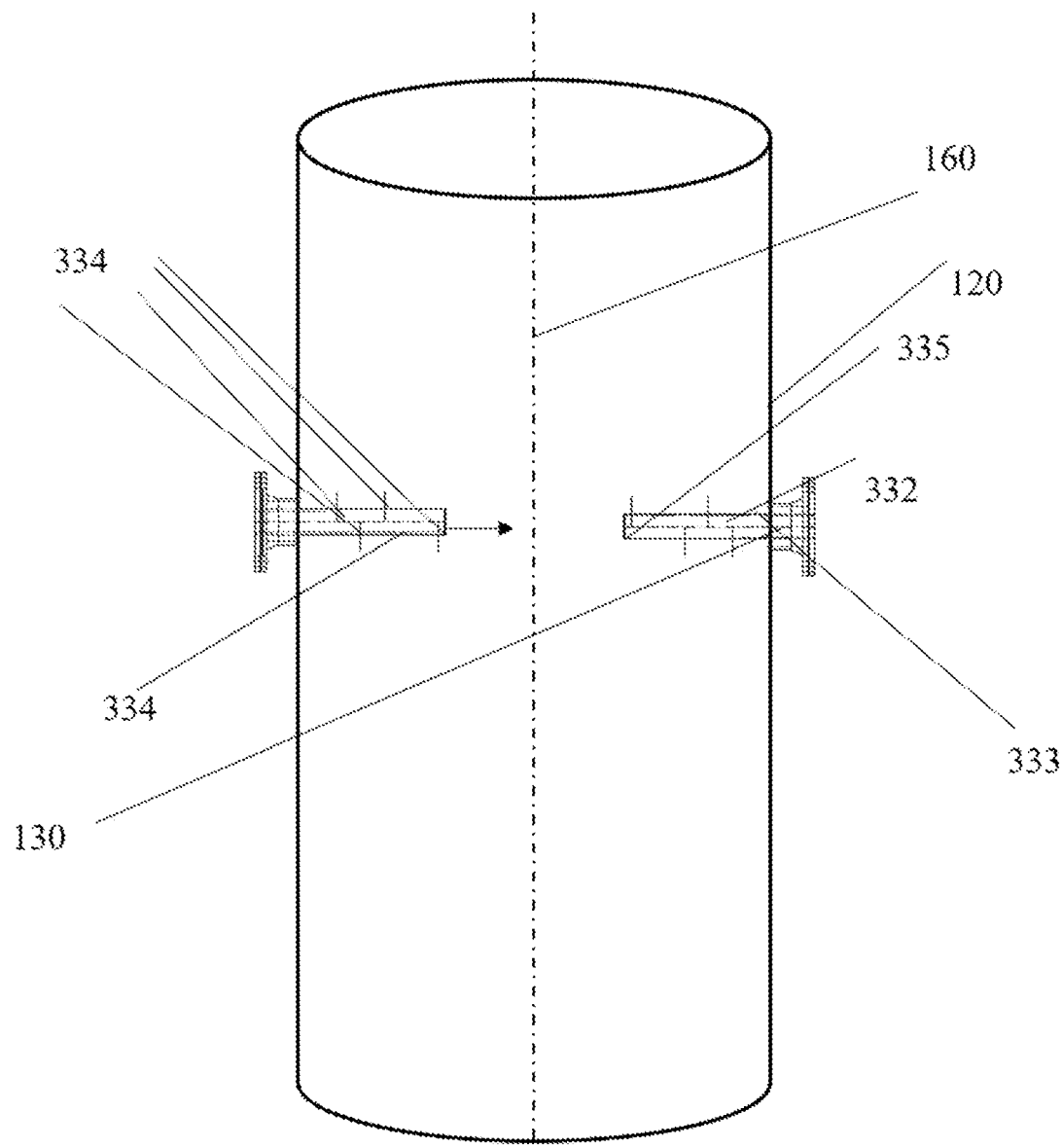
FIG. 1B shows a bioreactor system downcomer section depicting orientation of the liquid distributors in the downcomer section of the bioreactor in accordance with one embodiment of the disclosure.

In accordance with the disclosure, the liquid distributors 130 longitudinally extend from a wall of the downcomer section 120 (See FIGS. 1B, 2, 3, 4) and terminate at a closed end 335 proximate to a center vertical axis 160 of the downcomer section 120. Each liquid distributor 130 includes a circular pipe conduit 332 comprising a plurality of liquid injection apertures 334 along the circular pipe conduit. The liquid injection apertures inject at least one liquid for distributing to at least a portion of a cross-sectional area of the downcomer section. As shown in FIG. 1B, the circular pipe conduit 332 and the liquid injection apertures 334 are positioned in a plane which is perpendicular to the center vertical axis 160 of the downcomer section 120. In some embodiment shown in FIG. 1, the downcomer section 120 includes two sets of liquid distributors 130, each set being radially spaced apart from one another.

Figure 2:
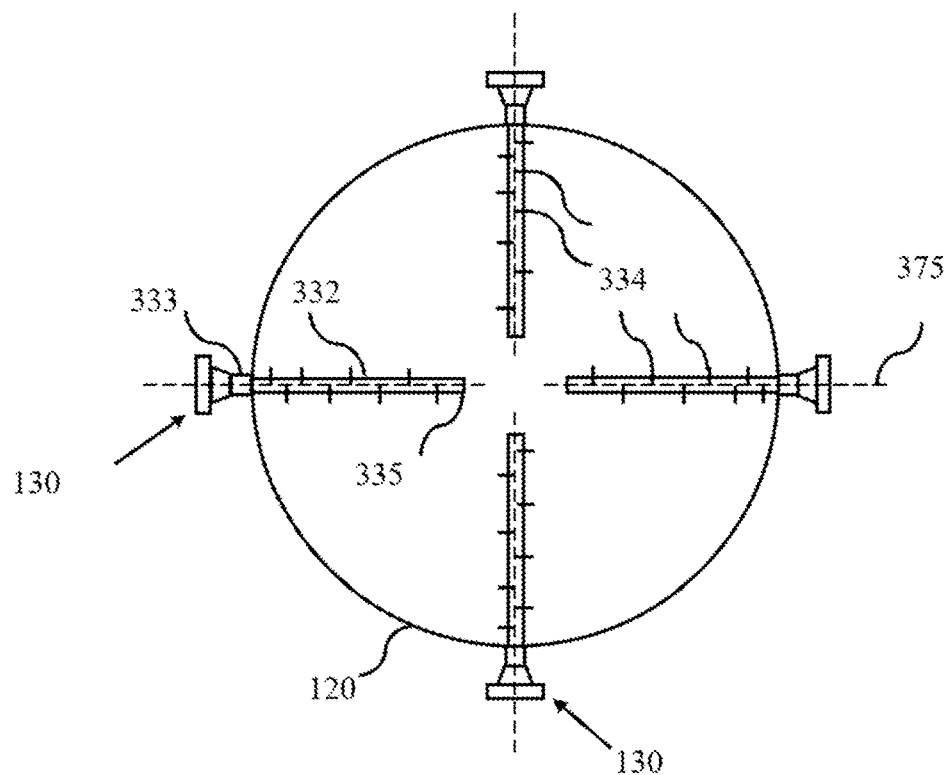
FIG. 2 shows a cross-sectional view of the downcomer section of the bioreactor comprising four liquid distributors, in accordance with another embodiment of the disclosure.
Figure 3:
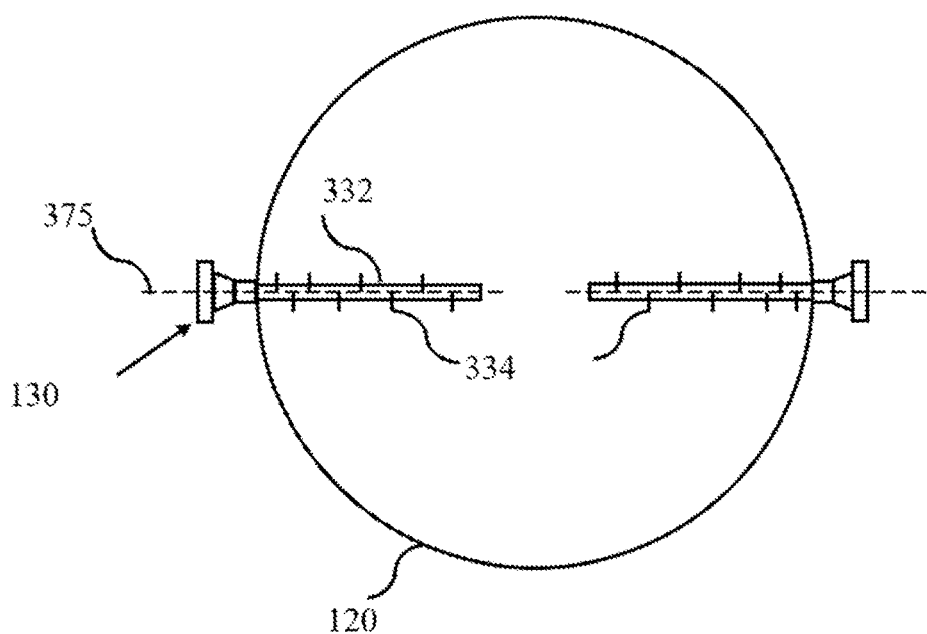
FIG. 3 shows a cross-sectional view of the downcomer section of the bioreactor comprising two liquid distributors, in accordance with yet another embodiment of the disclosure.

FIG. 2 shows a cross-sectional view of the downcomer section 120 of the bioreactor comprising four liquid distributors in accordance with another embodiment of the disclosure. Each liquid distributor 130 is radially spaced apart at about 90° from each other. Accordingly, each liquid distributor 130 distributes the liquid to cover at least 25% of the cross-sectional area of downcomer section 120. FIG. 3 shows a cross-sectional view of the downcomer section 120 comprising two liquid distributors in accordance with yet another embodiment of the disclosure. Each liquid distributor 130 is radially spaced apart at about 180° from each other. Accordingly, each liquid distributor 130 distributes the liquid to cover at least 50% of cross-sectional area of the downcomer section 120. The number of liquid distributors may be at least 1, or at least 2, or at least 4, or at least 6, or at least 8, or at least or at least 12. In various embodiments, each liquid distributor 130 distributes the liquid to cover a certain percent cross-sectional area of the downcomer section 120. For example, at least 100%, or at least 50%, or at least 25%, or at least 16.7%, or at least 12.5%, or at least 10%, or at least 8.4%. When more than one liquid distributors 130 are used, they are radially spaced apart by at least 180° (2 liquid distributors), or at least 90° (4 liquid distributors), or at least 60° (6 liquid distributors), or at least 45° (8 liquid distributors), or at least 36° (10 liquid distributors), or at least 30° (12 liquid distributors).

Figure 4:
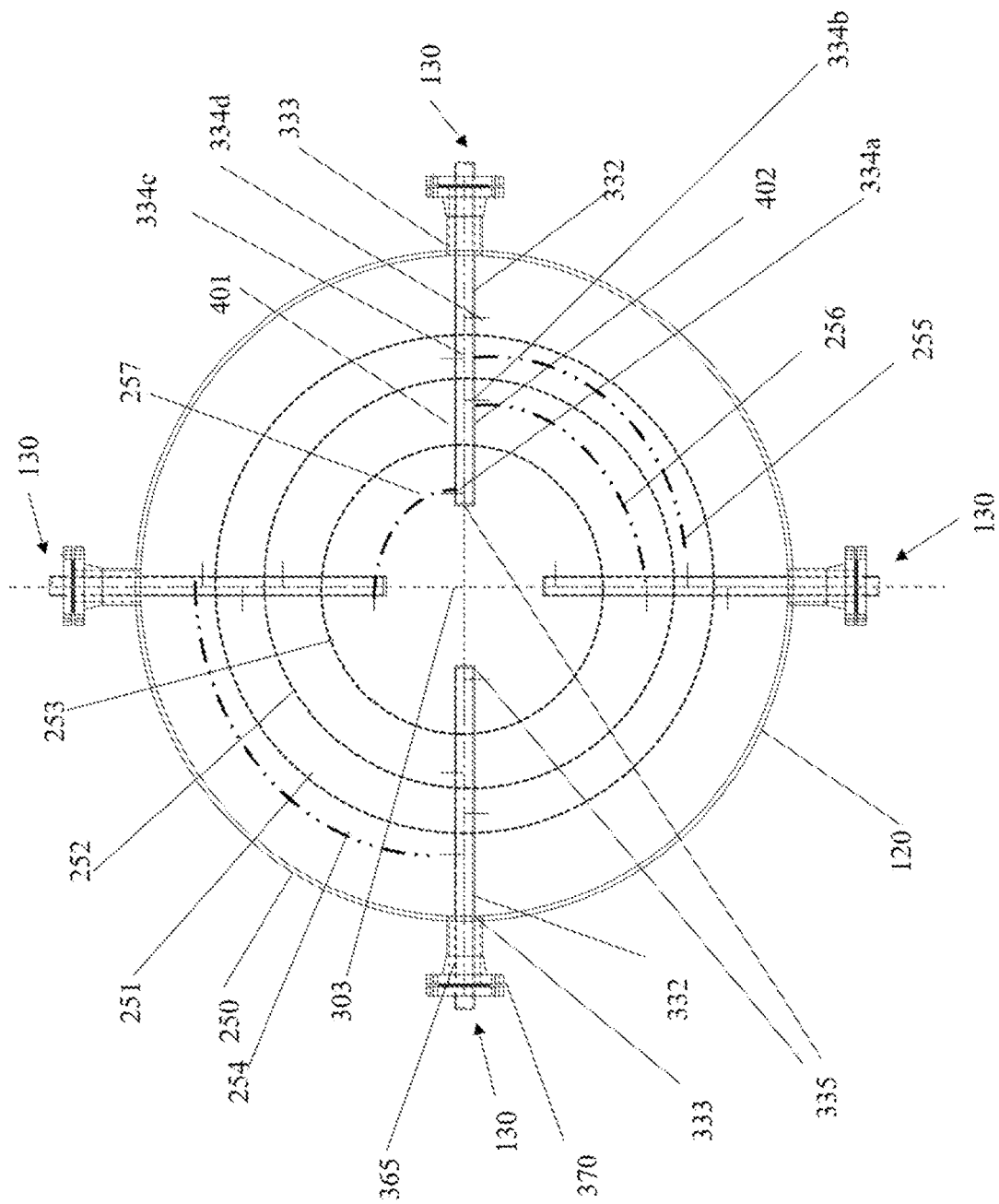
FIG. 4 shows a cross-sectional view of the downcomer section of the bioreactor further depicting details of the liquid distributor in an exemplary liquid distributor arrangement in accordance with still another embodiment of the disclosure.

FIG. 4 shows a cross-sectional view of the downcomer section 120 of the bioreactor further depicting details of the liquid distributor 130. Although FIG. 4 shows an embodiment with four (4) liquid distributors, each liquid distributor 130 is the same as all the other liquid distributors regardless of the number of liquid distributors used in any embodiment. The circular pipe conduit 332 begins at a proximal end 335 from the center vertical axis 160 of the downcomer 120 and terminates at a distal end 333 from the center vertical axis 160 (See FIG. 4 and FIG. 1B). Generally, the circular pipe conduit of each liquid distributor includes a closed end and a connector end. The closed end is sealed and allows discharge of the liquid via the liquid injection apertures 334 on the liquid distributor 130. The connector end includes a connector 365 to secure the circular pipe conduit with a flange 370 to the wall of the bioreactor. In one embodiment of the disclosure, the proximal end 335 of the liquid distributor 130 corresponds to the closed end of the distributor and the distal end of the liquid distributor 333 corresponds to the connector end of the distributor. The liquid injection apertures are therefore positioned from the closed end (proximal end) to the connector end (distal end) along the circular pipe conduit 332.

As the liquid injection apertures 334 are positioned in a plane perpendicular to the centre vertical axis 160 of the downcomer section 120, the liquid discharged from the liquid injection apertures 334 impart a cross-flow momentum to the vertically flowing fermentation broth. The cross-flow momentum imparted to the fermentation broth is beneficial for effective distribution of the liquid with the fermentation broth throughout the cross-sectional area of the downcomer section 120. In various embodiments, the liquid includes, but is not limited to, $NH_4OH$, $KOH$, nutrients, phosphoric acid, or any combinations thereof.

Liquid injection apertures 334 inject liquid at a certain exit velocity therefrom to ensure uniform distribution of the liquid with the fermentation broth flowing vertically through the downcomer section 120. The exit velocity depends on the flow rate of the liquid through the liquid distributors 130, the number of liquid injection apertures 334 in each circular pipe conduit 332, the number of liquid distributors, and the total area of the liquid injection apertures. In some embodiments, the exit velocity of the liquid may be from about 0.5 m/s to about 1.2 m/s. In various embodiments, the exit velocity may be for example, from about 0.5 m/s to about 0.7 m/s, or from about 0.7 m/s to about 0.9 m/s, or from about 0.9 m/s to about 1.2 m/s. Generally, the number of apertures in each circular pipe conduit of the liquid distributor varies from 4 to 10 apertures. In various embodiments, the number of the liquid injection apertures 334 arranged in the conduit 332 may be at least 4, or at least 6, or at least 8, or at least 10. Generally, the liquid injection apertures 334 are circular, but can also have other shapes including, but not limited to, square, rectangular. In general, each liquid injection aperture 334 has a minimum opening of 3 mm to avoid plugging. In some embodiment, each of the liquid injection aperture opening can vary from about 3 mm to about 11 mm. In various embodiments, each of the liquid injection aperture opening can be for example, from about 3 mm to about 5 mm, or from about 5 mm to about 7 mm, or from about 7 mm to about 9 mm, or from about 9 mm to about 11 mm. The exit velocity can be calculated as $V_e = Q/A$, where A (total area of liquid injection apertures)$= (\pi/4)*d^2*n$; Q=flow rate of the liquid through all the liquid distributors 130, d=opening size of each of the liquid injection aperture, n=total number of the liquid injection apertures i.e., the number of the liquid injection apertures in each of the circular pipe conduit multiplied by the number of circular pipe conduits i.e., the liquid distributors. The liquid injection apertures 334a, 334b, 334c, 334d are positioned offset alternately on the top surface 401 and the bottom surface 402 of the circular pipe conduit 332. Such positioning of the apertures avoids mutual interference of the liquid injected from each of the apertures. By top and bottom surface of the circular pipe conduit is meant the top semicircle (half) and bottom semicircle (half) of the circular pipe conduit if it is bisected along its length. In an exemplary embodiment of FIG. 4, the liquid injection aperture 334a is positioned on the top surface of the circular pipe conduit, the liquid injection aperture 334b is positioned on the bottom surface of the circular pipe conduit and offset from liquid injection aperture 334a, the liquid injection aperture 334c is positioned on the top surface of the circular pipe conduit and so on.

Generally, uniform flow rate through each of the liquid injection aperture 334 is accomplished by maintaining relative variation of the average pressure drop $\Delta P_0$ across successive liquid injection apertures low compared to the overall pressure drop $\Delta P$ of the circular pipe conduit 332. When the total area of the liquid injection apertures 334 is small compared to the cross-sectional area of the conduit 332, maldistribution of flow across the liquid injection apertures is minimized. Generally, the total area of the liquid injection apertures 334 can be less than about 10% of the cross-sectional area of the circular pipe conduit 332. In various embodiments, the total area of the liquid injection apertures can be less than about 10%, or less than about 8%, or less than about 5% of the cross-sectional area of the circular pipe conduit 332.

The liquid injection apertures 334 are arranged such that the spacing between successive apertures decreases non-uniformly along the length of the circular pipe conduit from the proximal end 335 (i.e., the closed end) with respect to the center vertical axis of the downcomer section to the distal end 333 (i.e., connector end or downcomer section wall) with respect to the center vertical axis of the downcomer section. Such arrangement allows for the substantially equal distribution of the liquid across the cross sectional area of the downcomer section. Each liquid injection aperture injects liquid in such a manner that defines a circular or annular area of the downcomer. This circular or annular area is defined by one circle at a radius from the aperture to the vertical center axis and a second circle with a radius from the vertical center axis to the midpoint positioned between successive apertures (Refer FIG. 4 and FIG. 1B).

Looking to FIG. 4, the stream from liquid injection aperture 334a covers a circular or annular area defined by one circle at 257 (having radius $r_a$ from the downcomer centre 303) passing through the aperture 334a and a second circle 253 (having radius $r_1$ from the downcomer centre 303). Similarly, the stream from the liquid injection aperture 334b covers a circular or annular area defined by one circle at 256 (having radius $r_b$ from the downcomer centre 303) passing through the aperture 334b and a second circle 252 (having radius $r_2$ from the downcomer centre). Likewise, the stream from the liquid injection aperture 334c covers a circular or annular area defined by one circle 255 (having radius $r_c$ from the downcomer centre 303) passing through the aperture 334c and a second circle 251 (having radius $r_3$ from the downcomer centre). Ideally, the stream from the liquid injection aperture 334d should cover the circle 250 having radius $r_4$ which is the downcomer radius rDC. However, in actual operating condition, $r_4$ i.e., the distance of the most distal aperture 334d from the downcomer centre 303 can't be maintained exactly equal to the downcomer radius (rDC) to prevent momentum loss of the liquid that may be impinging on the downcomer section 120 wall. Such momentum loss may be for example, due to the boundary layer separation of the liquid impinging on the downcomer section wall, which in turn adversely affects distribution efficiency of the liquid throughout the cross-sectional area of downcomer 120. Generally, in some embodiment, the most distal aperture 334d is positioned at a distance about 50 mm away from the downcomer wall. In various embodiments, the distance of the most distal aperture 334d may be for example, from about 50 mm to about 55 mm, or from about 55 mm to about 60 mm, or from about 60 mm to about 65 mm, or from about 65 mm to about 70 mm from the downcomer wall. Therefore, the discharge from liquid injection aperture 334d covers a circular or annular area defined by one circle 254 (having radius $r_d$ from the downcomer centre 303) passing through the aperture 334d and a second circle 250 (having radius $r_4$ from the downcomer centre).

Generally, to ensure substantially even liquid distribution each annular area bounded between the two circles associated with each liquid injection aperture is substantially equal to the annular area associated with the subsequent injection aperture. Taking the example of four liquid injection apertures in FIG. 4, the annular area between the circles 253 (radius $r_1$) and 252 (radius $r_2$) associated with the aperture 334b, 252 (radius $r_2$) and 251 (radius $r_3$) associated with the aperture 334c, 251 (radius $r_3$) and 250 (radius $r_4$) associated with the aperture 334d is substantially equal the area of the circle 253 (radius $r_1$) associated with the aperture 334a. Therefore, $\pi r_4^2 - \pi r_3^2 = \pi r_3^2 - \pi r_2^2 = \pi r_2^2 - \pi r_1^2 = \pi r_1^2$. Resolving previous equation yields that $r_3$=0.866rDC, $r_2$=0.707rDC, $r_1$=0.5rDC. The term "substantially equal" as used herein means that the area between the circles 250 and 251, the area between the circles 253 and 252, the area between the circles 252 and 251 and the area of the circle 253 are at least 98% or, at least 99%, or at least 99.5%, or at least 99.8% equal.

Furthermore, the annular areas are equally divided to determine radial position of each of the liquid injection aperture. For example, aperture 334d (most distal aperture from the downcomer center) has a radial location set such that the annular area between the circles 250 and 251 is bisected into two equal areas. Therefore, $\pi r_4^2 - \pi r_d^2 = \pi r_d^2 - \pi r_3^2$. Similarly, the radial location of the aperture 334c is set by bisection of the annular area between the circles 251 and 252. Therefore, $\pi r_3^2 - \pi r_c^2 = \pi r_c^2 - \pi r_2^2$. Likewise, the radial location of the aperture 334b is set by bisection of the annular area between the circles 253 and 252. Therefore, $\pi r_2^2 - \pi r_b^2 = \pi r_b^2 - \pi r_1^2$. Radial location of the aperture 334a (most proximal aperture from the downcomer center) is given by $\pi r_1^2 - \pi r_a^2 = \pi r_a^2$. Since $r_1$, $r_2$, $r_3$, $r_4$ is previously calculated from the equation described above, the radial distance of each liquid injection aperture from the centre of the downcomer can be obtained as $r_a$=0.354rDC, $r_b$=0.612rDC, $r_c$=0.791rDC and $r_d$=0.935rDC.

Figure 5:
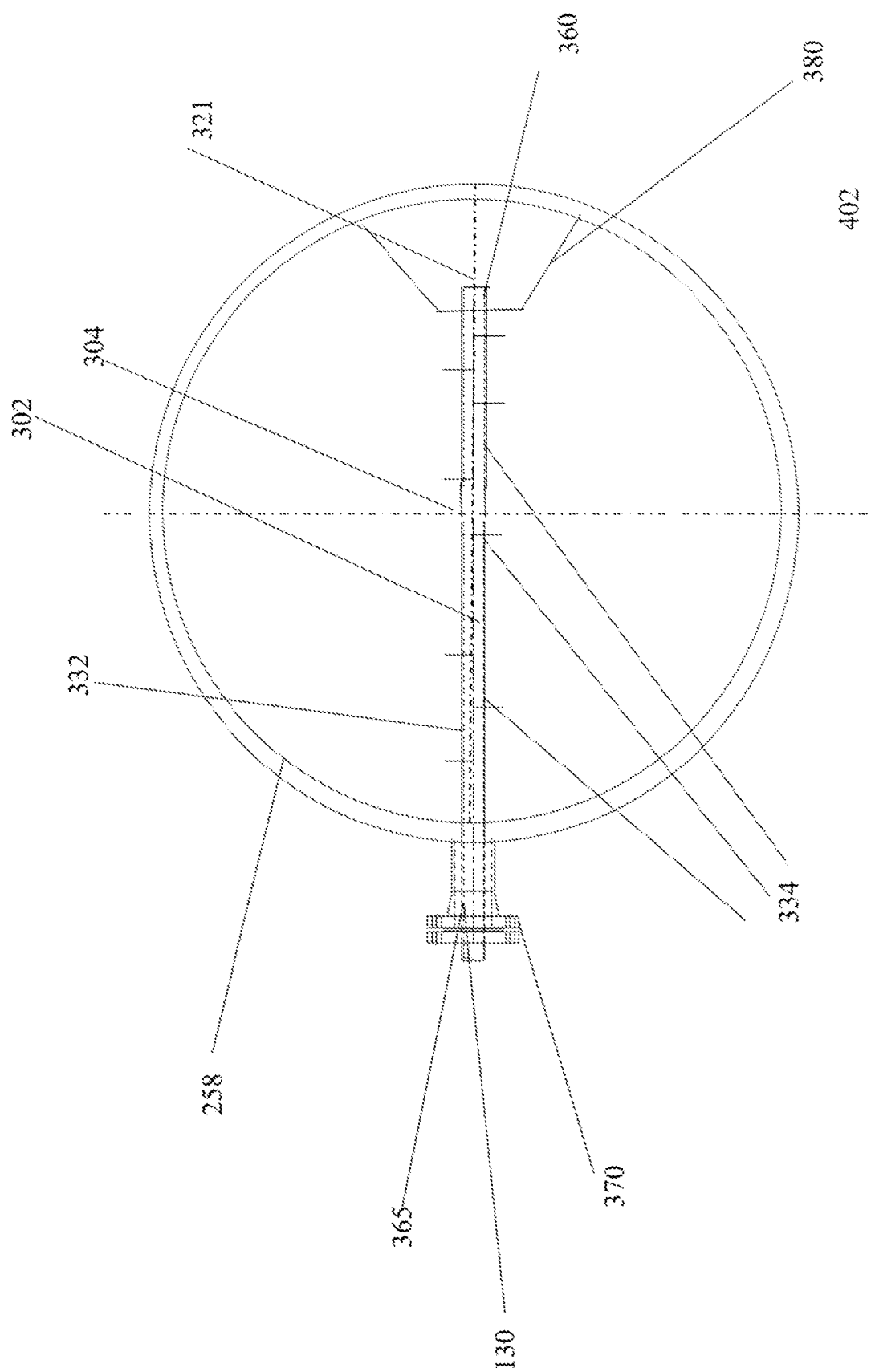
FIG. 5 shows a cross-sectional view of the downcomer section of the bioreactor depicting a single liquid distributor in accordance with yet another embodiment of the disclosure.

FIG. 5 shows a cross-sectional view of the downcomer section of the bioreactor depicting a single liquid distributor 130. The liquid distributor comprises a circular pipe conduit 332. The circular pipe conduit 332 is attached to the downcomer section wall 258 and includes a connector 365 to secure the conduit with a flange 370. The liquid distributor longitudinally extends from the downcomer section wall 258 substantially across the diameter 321 of the downcomer section which means that liquid distributor extends at least up to 95% or, at least 97%, or at least 98% of the diameter 321. The liquid distributor terminates at a closed end 360. The liquid distributor is secured to a support member 380 attached to the downcomer section wall 258 proximate to the closed end 360. A plurality of liquid injection apertures 334 are positioned along the circular pipe conduit 332 beginning at a midpoint 304 thereof corresponding to the center vertical axis of the downcomer section. (See FIG. 5 and FIG. 1B). The liquid injection apertures 334 are arranged such that the spacing between successive liquid injection apertures decreases non-uniformly along the length of the circular pipe conduit from the midpoint 304 of the circular pipe conduit 332 to both the closed end 360 of the circular pipe conduit and to the downcomer section wall 258. In some embodiment, the circular pipe conduit includes a dual pipe configuration (not shown) to enhance mechanical rigidity of the conduit.

The liquid injection apertures in the one distributor are arranged in a plane perpendicular to the center axis of the downcomer wall as described above. Also as described above the liquid injection apertures are alternately positioned and offset on the top and bottom of the circular pipe conduit. The liquid injection apertures are located along the circular pipe conduit from the center axis of the downcomer to the downcomer wall and closed end in the same way as described above in order to obtain substantially equal circular or annular areas of liquid distributions.

Having multiple liquid injection apertures arranged in accordance with the arrangement such that stream exiting one aperture covers an annular area substantially equal to the annular area covered by a successive aperture provides uniform distribution of the liquid with the fermentation broth flowing through the downcomer section. Such uniform distribution is beneficial to minimize undesired concentration zones of the liquid built up in the downcomer section 120 cross-sectional area.

Recitation of ranges of values herein are merely intended to serve as a shorthand method of referring individually to each separate value falling within the range, unless otherwise indicated herein, and each separate value is incorporated into the specification as if it were individually recited herein. For example, unless otherwise indicated, any concentration range, percentage range, ratio range, integer range, size range, or thickness range is to be understood to include the value of any integer within the recited range and, when appropriate, fractions thereof (such as one tenth and one hundredth of an integer).

All methods described herein can be performed in any suitable order unless otherwise indicated herein or otherwise clearly contradicted by context. The use of any and all examples, or exemplary language (i.e., "such as") provided herein, is intended merely to better illuminate the disclosure, and does not pose a limitation on the scope of the disclosure unless otherwise claimed. No language in the specification should be construed as indicating any non-claimed element as essential to the practice of the disclosure.

Embodiments of this disclosure are described herein. Variations of those embodiments may become apparent to those of ordinary skill in the art upon reading the foregoing description, and employment of such variations as appropriate, is intended to be within the scope as the disclosure may be practiced otherwise than as specifically described herein. Accordingly, this disclosure includes all modifications and equivalents of the subject matter recited in the claims as permitted by applicable law. Moreover, any combination of the above described elements in all possible variations thereof is encompassed by the disclosure unless otherwise indicated herein or otherwise clearly contradicted by context.

The invention claimed is:

1. A bioreactor system comprising:
(i) a riser section;
(ii) a downcomer section, containing fermentation broth, in fluid communication with the riser section;
(iii) at least two liquid distributors each comprising a circular pipe conduit longitudinally extending from a wall of the downcomer section and terminating at a closed end proximate to a center vertical axis of the downcomer section; and
(iv) the circular pipe conduit of each distributor comprising:
a plurality of liquid injection apertures along each of the circular pipe conduit beginning at a proximal end from the center vertical axis and terminating at a distal end from the center vertical axis;
(v) the liquid injection apertures, of each circular pipe conduit, arranged such that the spacing between successive apertures decreases non-uniformly along the length of the circular pipe conduit from the proximal end of the center vertical axis of the downer section to the distal end of the center vertical axis of the downer section; and
(vi) wherein the liquid injection apertures, on each distributor, alternate and are offset between a top and a bottom surface of the circular pipe conduit.

2. The system of claim 1, wherein the liquid injection apertures are positioned in a plane which is perpendicular to the center vertical axis of the downcomer section.

3. The system of claim 1, wherein the downcomer section comprises two liquid distributors radially spaced apart at about 180 degrees from each other.

4. The system of claim 1, wherein the downcomer section comprises four liquid distributors radially spaced apart at about 90 degrees from each other.

5. The system of claim 1, wherein each of the liquid injection aperture opening varies from about 3 mm to about 11 mm.

6. The system of claim 1, wherein the number of apertures on each distributor varies from 4 to 10 apertures.

7. A liquid distributor comprising:
a circular pipe conduit comprising a plurality of liquid injection apertures, the conduit comprising a closed end and a connector end wherein the liquid injection apertures are arranged from the closed end of the circular pipe conduit to the connector end of the circular pipe conduit, the spacing between successive apertures decreases non-uniformly from the closed end to the connector end of the circular pipe conduit, and wherein the liquid injection apertures alternate and are offset between a top and a bottom surface of the circular pipe conduit.

8. The liquid distributor of claim 7, wherein the connector end comprises a connector secured to a flange.

9. The liquid distributor of claim 7, wherein each of the liquid injection aperture opening varies from about 3 mm to about 11 mm.

10. The liquid distributor of claim 7, wherein the number of apertures varies from 4 to 10 apertures.

11. A bioreactor system comprising:
(i) a riser section;
(ii) a downcomer section, containing a fermentation broth, in fluid communication with the riser section; and
(iii) a liquid distributor comprising a circular pipe conduit attached to a downcomer section wall and longitudinally extending from the downcomer section wall across substantially the entire diameter of the downcomer and terminating at a closed end and secured to a support member attached to the downcomer section wall proximate to the closed end;
(iv) the circular pipe conduit comprising:
a plurality of liquid injection apertures along the circular pipe conduit beginning at a midpoint of the circular pipe conduit, corresponding to the center vertical axis of the downcomer section, the liquid injection apertures arranged such that the spacing between successive liquid injection apertures decreases non-uniformly along the length of the circular pipe conduit from the midpoint of the circular pipe conduit to both the closed end of the circular pipe conduit and to the downcomer section wall to which the conduit is attached, and further wherein the liquid injection apertures alternate and are offset between a top and a bottom surface of the circular pipe conduit.

12. The system of claim 11, wherein the liquid injection apertures are positioned in a plane which is perpendicular to the central vertical axis of the downcomer section.

13. The system of claim 11, wherein each of the liquid injection aperture have an opening from about 3 mm to about 11 mm.

\* \* \* \* \*